US006821400B2

(12) United States Patent
Jaeger

(10) Patent No.: US 6,821,400 B2
(45) Date of Patent: Nov. 23, 2004

(54) ELECTROCHEMICAL SENSOR WITH INCREASED REPRODUCIBILITY

(75) Inventor: Gérard Jaeger, Blonay (CH)

(73) Assignee: Asulab S.A., Marin (CH)

(*) Notice: Subject to any disclaimer, the term of this patent is extended or adjusted under 35 U.S.C. 154(b) by 242 days.

(21) Appl. No.: 09/874,035

(22) Filed: Jun. 6, 2001

(65) Prior Publication Data

US 2001/0050228 A1 Dec. 13, 2001

(30) Foreign Application Priority Data

Jun. 7, 2000 (EP) ............................................. 00202008

(51) Int. Cl.[7] ........................................... G01N 27/327
(52) U.S. Cl. ............................. 204/403.02; 204/403.03; 204/403.04
(58) Field of Search ..................... 204/403.01, 403.02, 204/403.03, 403.04

(56) References Cited

U.S. PATENT DOCUMENTS

| 5,378,628 A | * | 1/1995 | Gratzel et al. | ......... 204/403.14 |
| 5,395,504 A | * | 3/1995 | Saurer et al. | ........... 204/403.03 |
| 5,502,396 A | * | 3/1996 | Desarzens et al. | ..... 204/403.02 |
| 6,168,699 B1 | * | 1/2001 | Frenkel et al. | ......... 204/403.14 |

FOREIGN PATENT DOCUMENTS

| DE | 197 47 875 | 6/1999 |
| EP | 787 984 | 8/1997 |
| JP | 06 288964 | 10/1994 |

OTHER PUBLICATIONS

Machine translation of JP 06–288,964.*
Patent Abstracts of Japan, vol. 1995, No. 1, Feb. 28, 1995 for JP 06 288964.

* cited by examiner

*Primary Examiner*—Kaj K. Olsen
(74) *Attorney, Agent, or Firm*—Sughrue Mion, PLLC

(57) ABSTRACT

The invention concerns a sensor allowing the concentration of a constituent to be determined and being formed by a tongue of small dimensions including a thin plastic substrate (1) supporting at least two current conducting strips (4, 5) separated by a narrow insulating strip (3) of the substrate (1), said substrate (1) and said strips (4, 5) being covered with a plastic covering (2) into which are cut, at one end an opening (8) allowing portions of strip (4, 5) to appear for connection to an electronic apparatus and at the other end two windows (9a, 9b) separated by a strip (11) of the covering (2), said windows (9a, 9b) delimiting on the strips (4, 5) the useful surfaces of a reference electrode beneath a first window (9b) and a measuring electrode beneath a second window (9a) covered with a specific reactant. It is characterised in that at least the measuring window (9a) has an oblong contour in the direction of the tongue.

Application to a glucose sensor in which the specific reactant contains at least glucose oxidase (GOD) and a mediator.

5 Claims, 1 Drawing Sheet

ELECTROCHEMICAL SENSOR WITH INCREASED REPRODUCIBILITY

BACKGROUND OF THE INVENTION

The present invention concerns an electrochemical sensor in the shape of a tongue intended to measure, using a reactant which is deposited beforehand on its working electrode, the concentration of a constituent in a sample solution or liquid or natural or biological origin in a reproducible manner from one sensor to another sensor.

The invention concerns more particularly sensors of this type which are used for the medical follow-up of a patient requiring frequent measuring of a constituent in a biological body fluid so as to adapt a treatment as a function of a reference value, such as the blood glucose level for a person suffering from diabetes.

During the last ten years, the generally disposable electrochemical sensors, intended for biological measurements, have experienced considerable development aimed at improving qualities, such as sensitivity, reliability, speed of response or ease of use by a user. Generally speaking, these sensors are formed by an insulating support of small dimensions, supporting at least two conducting strips electrically separated and able to be connected at one end to an electronic measuring device, said conducting strips being covered with a film into which two windows are cut exposing portions of strip respectively forming the reference electrode and the working electrode on which there is immobilised a determined quantity of specific reactant of the constituent whose concentration one wishes to determine. After having deposited the sample to be analysed on the measuring zone, for example a drop of blood, the measurement is effected indirectly by exploiting an electric signal generated by the interaction between said specific reactant and said constituent.

This exploitation of the electric signal consists generally in conductometric, voltainmetric, amperometric, coulometric or polarographic measurements allowing an electronic measuring device to interpret said signal and to display the concentration of the constituent in a determined mode (mg/dl, mmol/l) directly on a screen. In order for the displayed value to always be the same for a determined concentration, the electric signal supplied by the sensor must not vary as a function of the sensor used, i.e. these sensors must be able to be manufactured at a low cost in series to be disposable via a method which nonetheless guarantees a high degree of reproducibility. The parameters which can be acted on are in particular the dosage precision of the various compounds involved in the composition of the specific reactant, the precision of the quantity of reactant deposited on the working electrode, and the precision of the useful surface of the electrodes, in particular the surface of the working electrode which is actually covered by the specific reactant. It is relatively easy to obtain a high level of precision for the composition of the reactant and for the quantity deposited on the working electrode. Following the teaching of European Patent No. 0 787 984, it is also possible to have a high level of precision as regards the useful surface of the electrodes by having conducting strips which pass through the windows without leaving any portion of the substrate apparent. However, the Applicant has noticed that it is relatively difficult to have a perfect reproducible covering of the useful surface of the working electrode by the specific reactant when it is applied by pipetting in windows of the current shapes, namely rectangular windows or windows in the shape of a half-moon, i.e. in both cases windows having contours with sharp angles.

The material into which the windows are cut is generally a hydrophobic material, such as polyethyleneterephtalate (PET). This hydrophobic phenomenon is in competition with the capillary properties of the specific reactant, so that when the desired quantity of specific reactant is deposited at the centre of the window by pipetting, it is not spread uniformly over the entire useful surface of the working electrode. In particular, very irregular covering is noted at the sharp angles.

In order to overcome this, it is possible to effect the deposition of the specific reactant via pipetting by starting by following the contour of the window as closely as possible the contour and/or by giving the pipette a certain inclination. It can easily be seen that such a method is not applicable to series manufacturing in which the sensors are manufactured in batches on substrates in a plate or strip shape prior to being cut to be packaged individually.

In order to make the contour of the window hydrophilic, pre-treatment with an alcohol has also been tried. Indeed, better wettability of the window is obtained, to the point that the specific reactant also spreads over the PET covering sheet. It is difficult, even impossible, to perform this hydrophilic treatment only in the vicinity of the vertical edges of the covering sheet.

SUMMARY OF THE INVENTION

The object of the invention is thus to overcome the drawbacks of this prior art by providing an electrochemical sensor wherein the useful surface of the working electrode is covered in a uniform and reproducible manner by a specific reactant of a constituent present in a solution or a liquid of natural or biological origin, as a result of a shape which is oblong in the direction of the tongue and given at least to the window delimiting the useful surface of the working electrode including said specific reactant.

BRIEF DESCRIPTION OF THE DRAWINGS

Other features and advantages of the invention will appear more clearly upon reading the following detailed description, concerning by way of illustrative and non limiting example an electrochemical sensor for determining a level of glucose in the blood, with reference to the annexed drawings; in which:

FIGS. 1 and 2 show an electrochemical sensor for measuring the level of glucose level in the blood, i.e. a sensor whose measuring electrode is coated with a specific reactant 10 the composition of which will be explained hereinbelow. This sensor has the shape of a thin tongue of small dimensions of a total thickness comprised between 0.40 and 0.80 mm, preferably approximately 0.60 mm, a width comprised between 6 and 12 mm preferably approximately 8 mm and a length of the order of 40 mm.

DETAILED DESCRIPTION OF THE INVENTION

Figure 1:
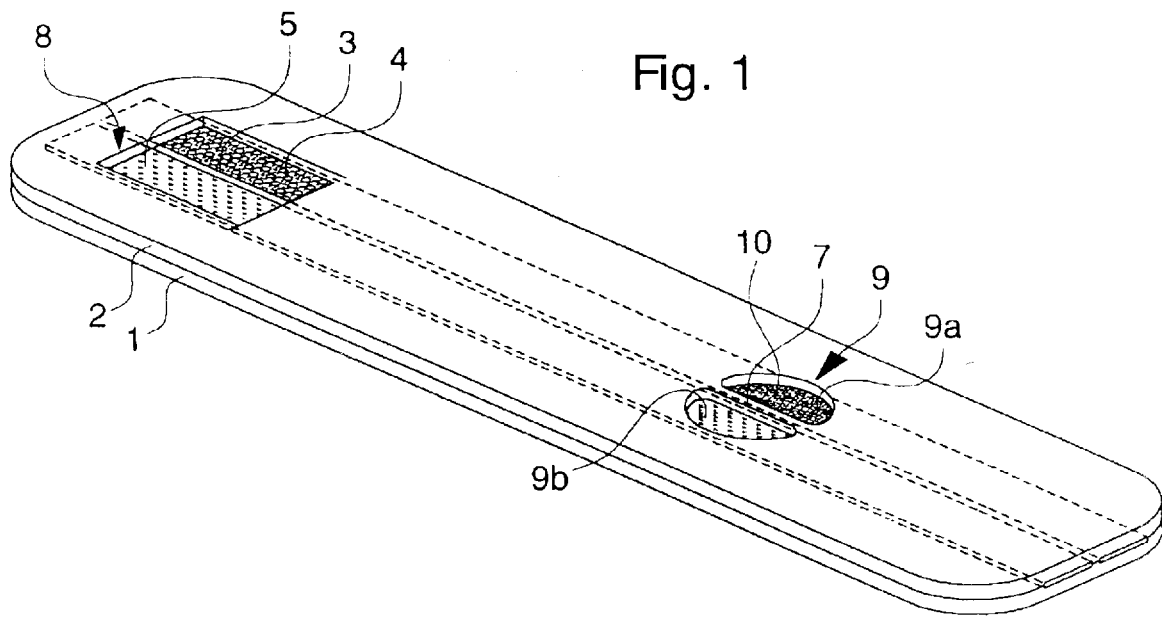
FIG. 1 shows in perspective a sensor according to the invention.

The sensor includes a thin insulating substrate 1, for example obtained from a sheet or a strip of polyethyleneterephtalate (PET). The substrate carries two conducting strips 4 and 5 which are electrically insulated by a narrow strip 3 of substrate 1. The nature of conducting strips 4, 5 and the way in which they are applied onto substrate 1 are well known to those skilled in the art. The preferred method within the scope of the present invention consists in hot rolling two insulating films having a metallised surface for conducting strip 4 which will form working electrode 9a and for conducting strip 5 which will form reference electrode 9b. These two metallised films can be identical or conversely have different metal coatings. For example, the well known pair Pt or Pd—Ag/AgCl can be used. The assembly is covered with an insulating covering 2 into which are cut two zones 8, 9 allowing portions of conducting strips 4, 5 to appear. A first zone 8, located at one end of the sensor, allows said conducting strips 4, 5 to be connected to the electronic measuring device. A second zone 9 constitutes the measuring zone on which a drop of blood to be analysed will be deposited. It includes two windows located respectively above portions of strips 4, 5, a first window 9a delimiting the working electrode and a second window 9b delimiting the reference electrode, without allowing any position of substrate 1 appear. These two windows 9a, 9b are separated by a strip 11 of insulating covering 2.

Figure 2:
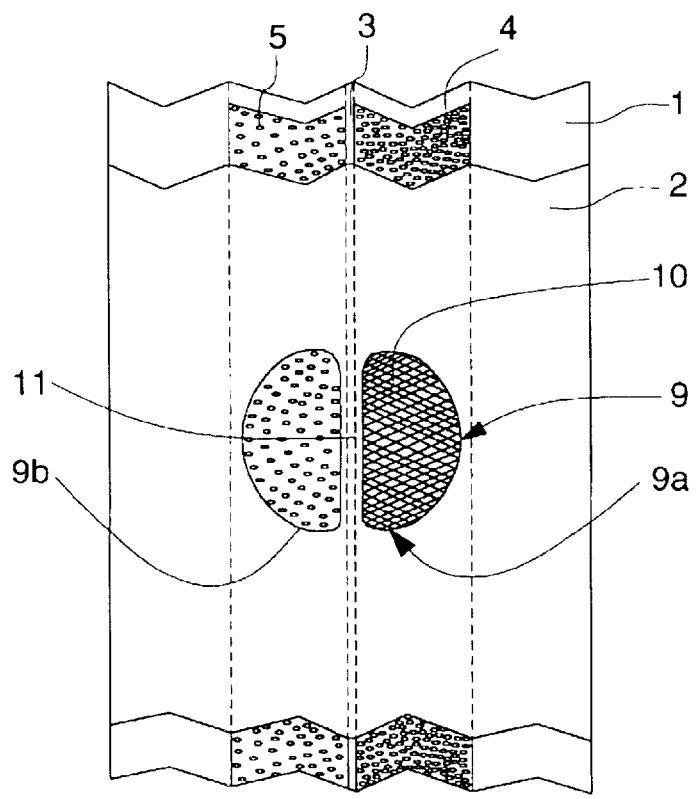
FIG. 2 shows an enlarged top view of the measuring zone of the sensor of FIG. 1.

The two windows 9a, 9b are characterised in that they have an oblong shape in the direction of the tongue. In the preferred embodiment shown in FIG. 2 it can be seen that windows 9a, 9b have a "coffee bean" configuration, i.e. inscribed in a circle so that a drop of blood deposited in this zone covers them perfectly and the ionic junction is facilitated by the closeness of the opposite edges. This configuration thus allows a determined quantity of specific reactant 10 to be deposited by pipetting substantially in the middle of measuring window 9a and perfect covering of the entire useful surface of the working electrode to be obtained without spreading or overflowing beyond said window. In the example chosen concerning the determination of a glucose level, the specific reactant includes in particular glucose oxide (GOD) and a mediator allowing the electrons to be transferred, for example one of the mediators described in U.S. Pat. No. 5,378,628, namely mono, bis or tris 2-2' ruthenium, osmium or vanadium bipyridines complexes in which at least one of the bipyridine ligands is substituted by at least an electron donor group.

When the windows are made by stamping, which forms the preferred embodiment, the formation of "angel hair" has however often been observed in the sharp angles, i.e. very fine filaments which can also be responsible for the poor distribution of specific reactant 10 at this location. With the curvilinear contour according to the invention, this drawback is completely eliminated.

The preceding description was made with reference to an electrochemical sensor for determining a glucose level, but those skilled in the art may, without departing from the scope of the invention, make the necessary adjustments for any other type of electrochemical sensor for determining or measuring other chemical or biological parameters.

What is claimed is:

1. An electrochemical sensor for determining the concentration of a constituent present in a solution or in a liquid of natural or biological origin, formed by a tongue including a thin plastic substrate supporting at least two current conducting strips separated by a narrow insulating strip of the substrate, said substrate and said conducting strips being covered with a plastic covering into which are cut, at one end, an opening allowing portions of said conducting strip to appear for connection to an electronic apparatus, and, close to the other end, two windows laterally separated by a strip of the plastic covering, said windows delimiting on the conducting strips the useful surfaces of a reference electrode beneath a first reference window and a measuring electrode beneath a second measuring window coated with a reagent of the constituent whose concentration one wishes to determine, wherein at least the measuring window has a rounded elongated contour along a length of the tongue, and wherein said strip of the plastic covering has substantially uniform lateral width over the length of the two windows.

2. An electrochemical sensor according to claim 1, wherein the reference window also has a rounded elongated contour along the length of the tongue.

3. An electrochemical sensor according to claim 2, wherein the measuring window and the reference window are symmetrical with respect to the narrow insulating strip separating the conducting strips, and have a coffee bean configuration.

4. An electrochemical sensor according to claim 1 for determining the level of glucose in the blood, wherein the reagent contains at least glucose oxidase and a chemical mediator able to transfer electrons.

5. An electrochemical sensor according to claim 4, wherein the mediator is selected from among the mono, bis or his 2-2' ruthenium, osmium or vanadium bipyridine complexes in which at least one of the bipyridine ligands is substituted by at least one electron donor group.

* * * * *